United States Patent [19]

Stanton

[11] 4,230,121
[45] Oct. 28, 1980

[54] ELECTRICAL BODY STIMULATOR

[75] Inventor: David J. Stanton, Anoka, Minn.

[73] Assignee: Medtronic, Inc., Minneapolis, Minn.

[21] Appl. No.: 7,306

[22] Filed: Jan. 29, 1979

[51] Int. Cl.$^3$ .................................................. A61N 1/36
[52] U.S. Cl. ..................................................... 128/422
[58] Field of Search ................. 128/419 PG, 421, 422

[56] References Cited

U.S. PATENT DOCUMENTS

| | | | |
|---|---|---|---|
| 3,518,996 | 7/1970 | Cortina | 128/422 |
| 3,521,641 | 7/1970 | Farensbach | 128/422 |
| 4,147,171 | 4/1979 | Greene et al. | 128/421 |
| 4,159,512 | 6/1979 | Geerling | 128/422 |

*Primary Examiner*—William E. Kamm

*Attorney, Agent, or Firm*—Schroeder, Siegfried, Ryan, Vidas, Steffey & Arrett

[57] ABSTRACT

An electrical body stimulator having particular utility for transcutaneous electronic nerve stimulation. Circuitry is provided which delivers a driving pulse, the stimulator output circuitry being responsive to the driving pulse duration for establishing at least one stimulation signal parameter in accordance therewith. In a preferred embodiment, the driving pulse generator includes an energy storage device and an oscillating power supply connected to the storage device for alternately charging and discharging the storage device. A dual state device responds to the charge level of the energy storage device and changes state in response to predetermined changes in the energy storage device charge level. The charging rate is alterable to alter the duration of the driving pulse.

10 Claims, 4 Drawing Figures

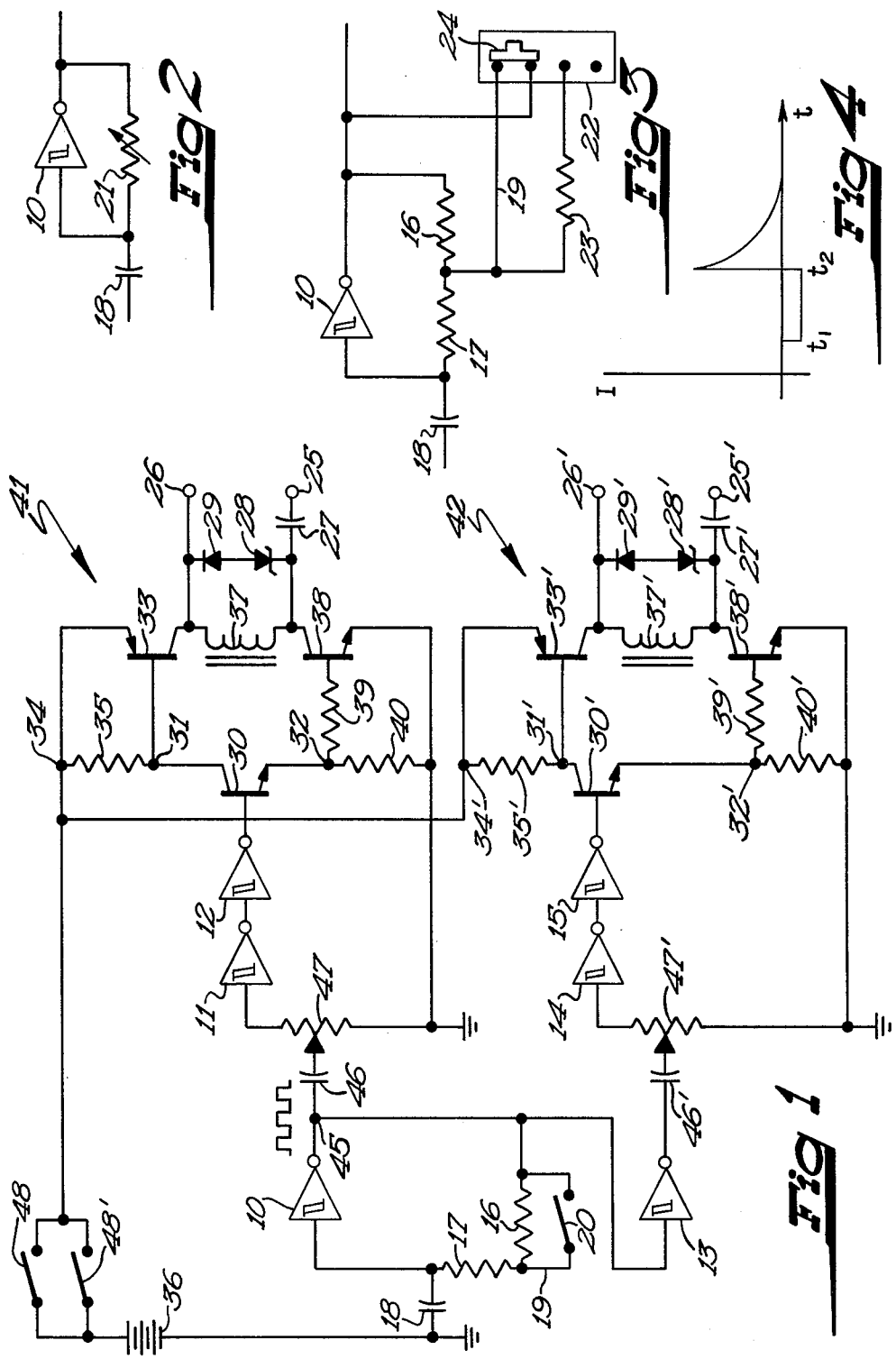

4,230,121

ELECTRICAL BODY STIMULATOR

DESCRIPTION

BACKGROUND OF PRIOR ART

The application of electrical signals to various portions of the body for such purposes as organ and nerve stimulation and pain alleviation is well known. Such signals have been applied transcutaneously by external stimulators as well as internally with implantable devices. When it can be effectively implemented, the use of transcutaneous stimulation eliminates the need for surgery.

Many transcutaneous stimulators are known to the prior art. For example, U.S. Pat. No. 3,817,254, issued June 18, 1974 to Donald D. Maurer for Transcutaneous Stimulator and Stimulation Method, shows such a system for organic pain suppression which delivers output pulses each having a plurality of frequency components concentrated within a specified frequency range. Other, more recent, devices are well known.

Among the problems encountered in transcutaneous stimulation are power surges delivered to the patient, which may result from failure or malfunction of the stimulator, and unnecessarily short battery life resulting from the use of inefficient components and circuit designs.

BRIEF SUMMARY OF THE INVENTION

The present invention provides an electrical body stimulator having particular utility for transcutaneous electronic nerve stimulation. The stimulator design protects the patient from potentially dangerous power surges resulting from component failures and maximizes power supply life by providing an efficient circuit design. In a preferred embodiment, a driving pulse generator delivers driving pulses to an output circuit, the output circuit being responsive to driving pulse duration to establish at least one stimulation signal parameter in accordance therewith. The driving pulse generator comprises an energy storage device and an oscillating power supply connected to the storage device which alternately charges and discharges the storage device. A dual state device responds to the charge level of the storage device and changes state in response to predetermined changes in the storage device charge level. The driving pulse duration is alterable to alter the output pulse parameter. The present invention may be a single or multi-channel system.

BRIEF DESCRIPTION OF THE DRAWINGS

FIG. 1 illustrates a preferred embodiment of the present invention.

FIG. 2 illustrates a modification of the embodiment of FIG. 1.

FIG. 3 illustrates a further modification of the embodiment of FIG. 1.

FIG. 4 illustrates the wave form of the output signal of the embodiment of FIG. 1.

DETAILED DESCRIPTION OF THE INVENTION

FIG. 1 illustrates a preferred embodiment of the present invention including six Schmitt triggers 10-15 having inverted outputs. Schmitt triggers 10-15 are of a type known to the prior art and may be equivalent or similar to industry types 54C14 or 40106. Such devices are commonly packaged six to an integrated circuit and the indicated types have hysteresis. However, as will be understood from the following description, hysteresis is necessary only for Schmitt trigger 10, 11 and 14. Indeed, Schmitt triggers 12, 13 and 15 may be replaced by inverters of conventional design.

Schmitt trigger 10 forms an oscillator with resistors 16 and 17 and capacitor 18, in known manner. A shunt 19 having a switch 20 is connected across resistor 16 to selectively alter the frequency of the oscillator. With the configuration illustrated in FIG. 1, the frequency of the oscillator may be established at one of two values. Alternative oscillators are illustrated in FIGS. 2 and 3 wherein like elements are given like reference numeral. In FIG. 2, a potentiometer 21 replaces resistors 16 and 17 and shunt 19 to provide a continuous frequency variation. In FIG. 3, a three position slide switch 22 replaces switch 20 and an additional resistor 23 is provided. The switch 22 has a slide 24 which selectively connects adjacent terminals of the switch. For example, in the illustrated position the top two terminals are connected to connect the shunt across resistor 16. In the middle position, resistors 16 and 23 are connected in parallel while in the bottom position, the shunt 19 and resistor 23 are not connected in the circuit.

The embodiment of FIG. 1 is a dual channel device employing output circuitry of known design, the channels being designated generally at 41 and 42 in FIG. 1. Terminals 25 and 26 of channel 41 are adapted for connection to electrodes suitable for transcutaneous stimulation. An output capacitor 27 is provided to prevent iontophoresis, in known manner, while diodes 28 and 29 limit the output voltage to a safe level when the illustrated embodiment is operated open circuit or with a high impedance load.

A transistor 30 has its base connected to the output of Schmitt trigger 12, its collector connected to a junction 31 and its emitter connected to a junction 32. Junction 31 is connected to the base of a transistor 33 and to a junction 34 via resistor 35. Junction 34 is connected to the emitter of transistor 33 and, via switch 48, to the positive terminal of a power source, such as batteries, 36. The collector of transistor 33 is connected to terminal 26 and an inductor 37. Terminal 32 is connected to the base of a transistor 38 via resistor 39 and to ground via resistor 40. The emitter of transistor 38 is connected to ground while its collector is connected to the terminal 25 via capacitor 27 and directly to the inductor 37.

The output circuit elements of channel 42 correspond directly to elements 25-35 and 37-40 of channel 41 and are given like primed reference numerals in FIG. 1.

A high signal applied to the base of transistor 30 will turn it on causing transistors 33 and 38 to turn on and apply a pulse to the inductor 37, the pulse having a width determined by the duration of the signal applied to the base of transistor 30 and an amplitude established by the power source 36. This is the time period from $t_1$ to $t_2$ illustrated in FIG. 4. The pulse applied to the inductor 37 causes a flux field in inductor 37. On removal of the pulse, on removal of the signal at the base of transistor 30, the flux field collapses producing a current spike whose amplitude is proportional to the magnitude of the flux field. This is the spike originating at time $t_2$ in FIG. 4. Thus, the output circuit of channel 41 provides a stimulation signal having an amplitude established by the duration of the signal applied to the base of transistor 30. The characteristics of the inductor 37 determine the pulse width of the exponentially decaying spike while the inductor maintains a constant current amplitude as skin impedance varies from about 100 to about 1000 Ohms. If only single channel operation is desired, one of transistors 33 and 38 may be eliminated, the use of both being required only during multi-channel operation to provide isolation by preventing the establishment of unwanted stimulation paths. The output circuit elements 25'-35' and 37'-50' of channel 42 operate identically to like elements of unprimed reference numeral in channel 41.

The remaining circuit elements, together with Schmitt triggers 11-15, provide the driving pulse for the output circuit of channels 41 and 42. The output of the oscillator is illustrated adjacent junction 45 and is a square wave. The junction 45 is connected to the wiper of a potentiometer 47 via capacitor 46. Potentiometer 47 is connected to the input of Schmitt trigger 11 and to ground. The junction 45 is also connected to the input of Schmitt trigger 13, Schmitt trigger 13 functioning as an inverter.

The output of Schmitt trigger 13 is connected to a capacitor 46' which is connected to the wiper of a potentiometer 47'. Potentiometer 47' is connected to the input of Schmitt trigger 14. Switches 48 and 48' are power switches with switch 48 being associated with potentiometer 47 and switch 48' being associated with potentiometer 47', in known manner, such that they cannot be opened unless their associated potentiometer is turned fully down. This assumes that closing of one of switches 48 and 48' will not result in an undesireable high energy output when the unit is turned on. Also, the manner in which potentiometers 47 and 47' are connected provide a safe failure mode. That is, failure of the wiper will result in a not output condition. That same condition results in the event that capacitor 46 or capacitor 46' should open. Again elements of like primed and unprimed reference numeral in channels 41 and 42 function identically.

In operation, and with reference to channel 41 with switch 48 in the closed position, Schmitt trigger 10 functions as a power supply for capacitor 46 during the positive half cycles of its oscillations. In essence, the oscillator functions as an oscillating power supply to alternately charge and discharge capacitor 46. Charging current for capacitor 46 passes through a portion of the resistor 47 and its wiper. As capacitor 46 begins charging, Schmitt trigger 11 has a high input voltage which remains above its low input threshhold voltage for a period of time determined by the capacitance of capacitor 46 and the position of the wiper of potentiometer 47. This results in a low output from Schmitt trigger 11 which is inverted by Schmitt trigger 12 to apply a high signal to the base of transistor 30 causing it and transistors 33 and 38 to turn on. As capacitor 46 continues charging, the signal applied to the input of Schmitt trigger 11 decreases and eventually falls below its low input threshhold voltage. At that time, the output of Schmitt trigger 11 goes high, is inverted by Schmitt trigger 12 resulting in a turn-off of transistors 30 and transistors 33 and 38 and the delivery of the spike output signal illustrated in FIG. 4. During the negative half cycles of the oscillator's oscillations, capacitor 46 will discharge through Schmitt trigger 10. Thus, the oscillator, capacitor 46, potentiometer 47 and Schmitt triggers 11 and 12 generate a driving pulse for the output circuit, the duration of that driving pulse establishing the output signal amplitude. Driving pulse duration is altered by moving the wiper of potentiometer 47 to alter the time constant of the charge path of capacitor 46. The elements of channel 42 function identically. However, Schmitt trigger 13 functions as an inverter. Thus, the output signals from channel 42 alternate in time with those from channel 41.

Obviously many modifications and variations are possible in light of the above teaching. For example, Schmitt triggers 13-15 and all elements of primed reference numeral may be eliminated to provide a single channel unit. In this mode, one of transistors 33 and 38 may be eliminated, as noted above. Also, the utility of the present invention has been noted in the context of transcutaneous electronic nerve stimulation. The utility of the present invention is not limited to that context but may be usefully employed in other body stimulation contexts. It is therefore to be understood that, within the context of the appended claims, the invention may be practiced otherwise than as specifically described.

I claim:

1. In an electrical body stimulator of the type having driving pulse generating means and driving pulse responsive means, including output means, for providing body stimulation signals, the improvement wherein said driving pulse generating means comprises:
    energy storage means;
    oscillating power supply means connected to said energy storage means for alternately charging and discharging said energy storage means; and
    threshhold means including dual state means responsive to the charge level of said energy storage means for changing state in response to predetermined changes in said energy storage means charge, said driving pulse responsive means comprising means responsive to the period between changes of state of said dual state means for establishing the stimulation signal amplitude in accordance therewith.

2. The stimulator of claim 1 wherein said predetermined changes in charge level comprises the charging of said energy storage means to a level above a preselected level.

3. The stimulator of claim 1 further comprising means for altering the charging rate of said energy storage means.

4. The stimulator of claim 3 wherein said energy storage means comprises capacitance means, said charging rate altering means comprising variable resistance means.

5. The stimulator of claim 4 wherein said dual state threshhold means comprises Schmitt trigger means.

6. The stimulator of claim 5 wherein said oscillating power supply means comprises square-wave generator means.

7. The stimulator of claim 6 wherein said predetermined changes in charge level comprise a charging of said energy storage means to a level above a preselected level.

8. The stimulator of claim 1 wherein said energy storage means comprises capacitance means.

9. The stimulator of claim 1 wherein said dual state threshhold means comprises Schmitt trigger means.

10. The stimulator of claim 1 wherein said oscillating power supply means comprises square-wave generator means.

* * * * *